United States Patent [19]

Chabardes et al.

[11] Patent Number: 5,155,277
[45] Date of Patent: Oct. 13, 1992

[54] PROCESS FOR CONVERTING TERTIARY AMINE N-OXIDES TO ALDEHYDES

[75] Inventors: Pierre Chabardes, Sainte Foy Les Lyon; Serge Henrot, Saint Genis Laval; Claude Mercier, Lyons, all of France

[73] Assignee: Rhone-Poulenc Nutrition Animale, Commentry, France

[21] Appl. No.: 712,389

[22] Filed: Jun. 11, 1991

[30] Foreign Application Priority Data

Jun. 11, 1990 [FR] France ................................ 90 07224

[51] Int. Cl.$^5$ ............................................. C07C 45/00
[52] U.S. Cl. .................................... 568/436; 568/426; 568/449; 568/483
[58] Field of Search ............... 568/436, 455, 426, 449, 568/484, 483, 485

[56] References Cited

U.S. PATENT DOCUMENTS

| | | | |
|---|---|---|---|
| 4,447,649 | 5/1984 | Breuniger | 568/484 |
| 4,745,229 | 5/1988 | Otera et al. | 568/490 |

FOREIGN PATENT DOCUMENTS 209910 5/1909 Fed. Rep. of Germany ...... 568/436

OTHER PUBLICATIONS

Fish et al., American Chemical Society, Journal, vol. 78 pp. 3668–3671 (1956).
Craig et al., American Chemical Society, Journal, vol. 83, pp. 1871–1878.

*Primary Examiner*—Werren B. Lone
*Attorney, Agent, or Firm*—Finnegan, Henderson, Farabow, Garrett and Dunner

[57] ABSTRACT

A process for converting tertiary amine N-oxides to aldehydes by reacting tertiary amine N-oxides in the presence of a catalytic quantity of a vanadium containing compound.

35 Claims, No Drawings

PROCESS FOR CONVERTING TERTIARY AMINE N-OXIDES TO ALDEHYDES

BACKGROUND OF THE INVENTION

The present to a process for the conversion of N-oxides to aldehydes, and more particularly, to the conversion tertiary amine N-oxides to aldehydes. It further relates to the field of aldehyde synthesis.

In the prior art, the Polonowsky reaction has been used to convert tertiary amine N-oxides containing at least one methyl group to secondary amines and formaldehyde in the presence of an excess of acetic anhydride.

Takabe et al., Synthetic Communications, 13(4) 297–301, (1983) recognize the use of this reaction in terpene synthesis. U.S. Pat. No. 4,447,649 also recognizes the use of this reaction for the preparation of citral from N-dialkylgeranylamine N-oxide.

These prior art reactions, however, have the drawback that they consume excess acetic anhydride and do not permit recycling of the secondary amine. This twofold drawback constitutes a considerable impediment to exploitation of the process on an industrial level.

In an effort to remedy these drawbacks, various other converting agents, instead of acetic anhydride, have been proposed. Henbest et al., Amine Oxydation part I, 3035, (1957) uses $MnO_2$ Lecher et al., J. Am. Chem. Soc. 70, 3789, (1948) uses $SO_2$. Various metal salts have also been proposed.

Of particular interest is the work of Fish et al. in the J. Am. Chem. Soc., 78, 3668, (1956) on the rearrangements of N-oxides in the presence of ferric ions.

Finally, Ferris et al. in the J. Org. Chem. 33, 3493, (1968) and Craig et al. in the J. Am. Chem. Soc. 83, 1871, (1961) showed that it was possible to use metals other than iron, particularly transition metals such as ruthenium, osmium and vanadium. However, with respect to vanadium, only its activity with respect to the conversion of trimethylamine N-oxide was shown. Moreover, this reaction was performed only in a very dilute aqueous medium in the presence of very large quantities of transition metal. For example, vanadium oxydichloride ($VOCl_2$) was used in an amount of three times the amount of N-oxide. This cannot be regarded as catalysis and it leads to the formation of formic acid. Under these conditions the vast consumption of metal derivative, the very high acidity of the reaction medium (pH 1.5) and the high degree of dilution make it nearly impossible to use this process on an industrial basis. In addition, the process only provides average yields.

SUMMARY OF THE INVENTION

It has now been found possible to convert tertiary amine N-oxides to aldehydes and secondary amines in high yields by working in the presence of a catalytic quantity of one or more vanadium containing compounds. More particularly, in the presence of vanadium salts of high oxidation number. The process has the advantages of no acid formation and troublefree recovery of the secondary amine. Finally, the process can be carried out under advantageous pH and temperature conditions.

DETAILED DESCRIPTION OF THE INVENTION

The subject of the present invention relates to a process of converting tertiary amine N-oxides to aldehydes, characterized in that the reaction is performed in the presence of a catalytic quantity of one or more vanadium derivatives.

According to the present invention, the term "catalytic quantity" means that the mole ratio of vanadium derivative (reckoned as metal)/N-oxide is less than 1. Preferably, the process of the invention is performed in the presence of a solvent.

The tertiary amine N-oxides used in the present invention may be obtained from the corresponding amines by oxidation thereof in the presence of an oxidizing agent. It is possible to use hydrogen peroxide, alone or under carbon dioxide pressure, as exemplified in the process described in U.S. Pat. No. 4,247,480.

The tertiary amine N-oxides for use in the present invention preferably correspond to the general formula:

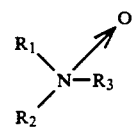

wherein $R_1$, $R_2$ and $R_3$, which may be the same or different, are selected from linear, branched or cyclic alkyl, allyl or alkenyl groups or benzyl groups, which groups, substituted or unsubstituted, contain 1 to 30 carbon atoms and optionally one or more hetero atoms, and wherein $R_1$ and $R_2$ together can form a ring.

Preferably, $R_1$ and $R_2$, which may be the same or different, are linear or branched alkyl groups containing 1 to 4 carbon atom. and which, together, can form a cyclic or a heterocyclic ring.

More preferably, $R_1$ and $R_2$, which may be the same or different, represent a methyl or ethyl group.

$R_3$ is preferably a substituted or unsubstituted, linear or branched allyl group having between 3 and 30 carbon atoms. $R_3$ may or may not contain a ring and may optionally contain one or more hetero atoms.

According to a second preference, $R_3$ is a substituted or unsubstituted benzyl group containing up to 30 carbon atoms. More preferably, the benzyl group may be substituted with alkyl, alkenyl, acyl, alkoxy, hydroxyl radicals, or radicals of the formulas CHO, $-R_4-COOR_5$ or $-R_4-X$, in which $R_4$ represents a valency bond or a divalent hydrocarbon radical, $R_5$ represents a hydrogen atom or an alkyl group and X denotes a halogen atom.

More preferably, $R_3$ is either an allyl group containing between 3 and 15 carbon atoms or a benzyl group in which the aromatic ring may be substituted.

The N-oxides of the formula are most preferably selected from N,N-dialkylprenylamine N-oxide, the N-oxide of N,N-dialkylgeranylamine or of its isomer N,N-dialkylnerylamine, N,N-dialkylbenzylamine N-oxide, N,N-dialkyl-(2,6,6-trimethyl-1-cyclohexenyl)methanamine N-oxide or N,N-dimethyl-ortho-hydroxybenzylamine N-oxide. For the purpose of this discussion, the term geranylamine is to be understood to mean a mixture of geranyl and nerylamine isomers.

The preferable vanadium derivatives or compounds for use in the process of the invention are salts of vanadium having all possible oxidation numbers. The salts of vanadium having high oxidation numbers are preferred and these include $V_2O_5$, $NH_4VO_3$ and alkyl vanadates such as triethanolamine orthovanadate (VOTEA) and octadecyl orthovanadate ($VO(OC_{18}H_{37})_3$), for an oxidation number of 5, and vanadyl acetylacetonate (VO(AcAc)$_2$) or vanadyl sulphate (VOSO$_4$) for an oxidation number of 4.

These vanadium derivatives may be used in suspension or on a support. When these derivatives are used on supports, the supports are preferably of the oxide type, more preferably aluminas or silicas. Alternatively, it is also possible to use charcoals or resins.

In one preferred embodiment the quantity of vanadium catalyst, set forth as the mole ratio of vanadium derivative (reckoned as metal)/N-oxide is preferably between 0.0001 and 0.5, and more preferably between 0.001 and 0.1.

Regarding the use of a solvent, the process may be carried out using a hydrocarbon, an ether, an ester, an alcohol, an aromatic solvent or a halogenated solvent. The hydrocarbons include, for example, pentane or hexane. Esters include, for example, ethyl acetate. Ethers include, for example, methyl tert-butyl ether. Halogenated solvents include, for example, methylene chloride or chlorobenzene. Aromatic solvents include, for example, toluene, xylene or benzene. Alcoholic solvents include, for example, methanol. The preceding list is merely illustrative and additional appropriate solvents would be within the skill of the practitioner.

The pH of the reaction medium is advantageously adjusted by adding an organic or inorganic acid or both. It is preferable to use acids such as acetic acid, benzoic acid, tartaric acid, formic acid or crotonic acid, alone or with the addition of an organic acid or an inorganic acid, such as, hydrochloric acid or sulphuric acid to a controlled pH. More preferably, a carboxylic acid is used. The pH of the medium is preferably adjusted to a value of between 4 and 7.

In addition the reaction medium preferably contains, per mole of N-oxide, between 0.05 and 2 litres of water and a volume of solvent of preferably between 0 and 20 litres, and more preferably between 0.5 and 10 litres.

The process of the invention is preferably performed at a temperature between room temperature and 150° C. The process is optionally performed under the autogenous pressure of the reactants.

The process of the invention makes it possible to recycle the secondary amines generated by the conversion reaction, to achieve a very good yield. In a particularly preferred embodiment, the process of the invention comprises reacting the tertiary amine N-oxide with the vanadium derivative or derivatives, and then recovering the aldehyde in the organic phase and the secondary amine in the aqueous phase.

Moreover, the process described above enables the preparation of unsaturated aldehydes directly from conjugated dienes an secondary amines, without isolating the reaction intermediates.

Accordingly another object of the invention includes a process for preparing unsaturated aldehydes, characterized in that the following steps are performed without isolating the reaction intermediates:

in a first step, a conjugated diene and a secondary amine are condensed, in a second step, the tertiary amine obtained in the first step is oxidized by means of an oxidizing agent, and in a third step, the tertiary amine N-oxide obtained in the second step is converted to an unsaturated aldehyde using the process described above.

The present invention thus provides an improved process for the synthesis of aldehydes. This process is especially well suited and efficacious for exploitation on an industrial scale.

The conjugated dienes for use in the process may be selected from substituted or unsubstituted, linear, branched or cyclic alkenyl groups containing 4 to 30 carbon atoms and optionally 1 or more hetero atoms.

The conjugated dienes for use in the invention preferably correspond to the same formula as the groups $R_3$ defined above. The conjugated dienes for use in the process of the invention thus may include, myrcene, isoprene, butadiene, farnesene or phytadiene.

In the present invention it is possible to use secondary amines of the formula $HNR_1R_2$ in which $R_1$ and $R_2$, which may be the same or different, are defined as above.

By way of example, the secondary amines may include diethylamine, which gives very good results.

The first step of this process may be carried out in several ways Generally, it is preferable to use a metal catalyst. The metals which are useful in this step of the invention are preferably alkali metals. More preferably, the alkali metals include metallic sodium, lithium or potassium. Generally, the catalysts described by Marata et al. in Nippon Kagaku Kaishi, 1233, (1982) are well suited to the process.

According to one embodiment of the present invention, it is possible to work in the presence of an activating agent in order to increase the yield or the rate of the reaction. More particularly, it is possible to add biphenyl or naphthalene to the alkali metal.

In a preferred embodiment of the invention, the mole ratio or amine to diene is preferably between 0.1 and 5, and more preferably between 0.5 and 2. It is preferable to work in the presence of a slight excess of amine.

The reaction is preferably performed at a temperature between room temperature and the refluxing temperature. It should be understood that the reaction conditions (temperature, reaction time, ratio of reactants, etc.) can be adapted by those skilled i the art to achieve the desired rate or yield.

Preferably, the mole ratio of catalyst to diene is between 0.001 and 0.1.

Before undertaking the second step of the process, it may be preferable to convert the alkali metal to the corresponding hydroxide or alkoxy compound by adding water or alcohol to the medium containing the alkali metal.

The second step comprises forming the tertiary amine N-oxide by means of an oxidizing agent.

Preferably, hydrogen peroxide is used as an oxidizing agent, optionally under a $CO_2$ atmosphere or pressure. More preferably, the quantity of hydrogen peroxide is selected so that the mole ratio of hydrogen peroxide to conjugated diene is close to the stoichiometric ratio. Still more preferably, a slight excess of hydrogen peroxide is used relative to the tertiary amine being formed.

The oxidation reaction can optionally be performed in the presence of a solvent, depending on the nature of the conjugated diene and amine used. When using a solvent, it is preferable to perform the oxidation in an alcoholic medium, for example, methanol or organic acid medium, for example, acetic acid, or in the presence of acetone. More preferably, a solvent which is compatible with the final step of the process is used.

The other parameters of the reaction (temperature, time, etc.) can be adapted by those skilled in the art in accordance with the diene and amine used and the desired reaction rate. The reaction temperature is most preferably between room temperature and 100° C.

The third step comprises converting the tertiary amine N-oxide formed during the preceding step to an unsaturated aldehyde, using a catalytic quantity of one or more vanadium derivatives according to the process described above.

This process for the synthesis of aldehydes provides a number of advantages at the industrial level. It is much simpler in its implementation than the processes of the prior art. Moreover, the process limits the number of items of apparatus necessary and avoids the need to handle intermediates, etc. This results in a gain in both time and economy. Moreover, the process makes it possible to regenerate the starting secondary amine, which can react again with a conjugated diene. Also, the side reactions occurring on the reaction intermediates, such as, rearrangement or the N-oxide according to the mechanism described by Meisenheimer, Ber. 52, 1667 (1919) are decreased, thereby improving the yields.

The present invention will be described more fully by means of the examples which follow. These examples are to be considered as illustrative and non-limiting.

EXAMPLE 1

A 1-liter three-necked round-bottomed flask equipped with a stirrer, a condenser, a dropping funnel and a thermometer was charged with:
0.2 g of $VOSO_4$ containing 22.75% of vanadium,
80 ml of 10% aqueous acetic acid solution, and
400 ml of methylene chloride.

The mixture was stirred and brought to reflux of the methylene chloride (38° C.). An aqueous solution of 13.6 g of N,N-diethylgeranylamine N-oxide at a concentration of 58%, dissolved in 40 ml of methylene chloride, was then added over a period of 11 minutes. The funnel was thereafter rinsed with 20 m of methylene chloride. The pH was 4.1.

The mixture was heated to 38° C. for 1 hour and cooled rapidly to room temperature. The organic phase was separated after settling had taken place and filtered rapidly through 250 of alumina having an activity grade of 4.

The assay of citral in the organic phase by gas chromatography gave a 75% yield relative to the N-oxide.

EXAMPLE 2

This example was carried out under the conditions described by Craig et al., discussed above. Independent of the implementation problems, it illustrates the low efficiency of the process.

A 3-liter three-necked round-bottomed flask equipped with a stirrer, a condenser, a dropping funnel and a thermometer was charged with:
2.04 liters of water
7.59 g of $VOSO_4 . 5H_2O$
The mixture was stirred and heated to 80° C., and
3.95 g of a solution of N,N-diethylqeranylamine N-oxide at a concentration of 58%, as in the preceding example, was then added. The pH was 2.4. The mixture was heated to 80° C. for 40 minutes, then cooled and extracted with 3×100 ml of methylene chloride.

The assay of citral in the organic phase as in Example 1 gave a yield of citral of only 2%. Geranic acid was not detected.

EXAMPLE 3

This example illustrates the advantageous recovery of the secondary amine when the process of the present invention is used.

A 1-liter three-necked round-bottomed flask equipped with a stirrer, a condenser, a dropping funnel and a thermometer was charged with:
13.8 g of N,N-diethylgeranylamine N-oxide at a concentration of 67.7% in aqueous solution,
0.2 g of $VOSO_4.5H_2O$,
50 ml of 10% aqueous acetic acid solution, and
100 ml of pentane.
The mixture was heated to reflux (33° C.) for 16 hours. After cooling, followed by separation after settling had taken place, the aqueous layer was extracted with 2×50 ml of pentane. After concentration, 5.5 g of a crude product was obtained, in which product the citral was assayed. The yield was 48.8%. Distillation of this crude product gave 2.8 g of citral or a yield of 45%.

The aqueous layer was taken to a pH of 10 by adding sodium hydroxide and then heated to 100° C. while distilling, which enabled 1.9 g of diethylamine to be recovered. This is equivalent to a 64% yield relative to the N-oxide introduced.

EXAMPLE 4

A reactor was charged with 7.5 ml of 10% acetic acid, 3.39 g of diethylgeranylamine N-oxide, 25 ml of pentane and an internal standard which allowed the yield of aldehyde formed to be determined at any instant. 0.05 g of $VOSO_4.5H_2O$ was dissolved in 5 ml of 10% acetic acid and the solution was run into the reactor over a period of 25 minutes while the temperature was maintained at 35° C. The course of the formation of citral over time was monitored by gas chromatographic assay.

| Time (min) | 35 | 75 | 120 | 240 | 300 | 360 | 420 | 450 | 480 |
|---|---|---|---|---|---|---|---|---|---|
| TY (%) | 1.6 | 8 | 14.3 | 31.9 | 41.9 | 47.4 | 52.6 | 54.3 | 55.3 |

TY = True Yield = number of moles formed over the number of moles introduced.

EXAMPLE 5

The reaction was performed in a 50-ml round-bottomed flask equipped with a condenser, a thermometer and a stirrer and possessing a septum for introduction of the N-oxide.

About $4 \times 10^{-5}$ mole of $VOSO_4$ (reckoned as metal) and an internal standard ($C_{11}$ hydrocarbon), which allows the yield of aldehyde to be determined at any instant, were charged into the flask. 4 ml of 10% acetic acid and 20 ml of chlorobenzene were then introduced and the temperature was adjusted to 60° C. $2 \times 10^{-3}$ mole of N,N-diethylgeranylamine N-oxide, diluted in 3 ml of chlorobenzene, was then introduced into the flask and the true yield of citral was measured by gas chromatography. The pH of the reaction was between 4 and 4.5.

The yield of citral was 46% in 45 minutes.

EXAMPLE 6

The procedure was the same as in Example 5, but the reaction was carried out in the presence of $NH_4VO_3$ instead of $VOSO_4$.

The yield of citral was 45% after 90 minutes.

EXAMPLE 7

The procedure was the same as in Example 5, but the reaction was carried out in the presence of vanadyl acetylacetonate instead of VOSO$_4$. The yield of citral obtained was 48% after 18 minutes.

EXAMPLE 8

The procedure was the same as in Example 5, but the reaction was carried out in the presence of octadecyl orthovanadate instead of VOSO$_4$. The yield of citral obtained was 42% after 45 minutes.

EXAMPLE 9

The procedure was the same as in Example 5, but the reaction was carried out in the presence of triethanolamine orthovanadate instead place of VOSO$_4$. The yield of citral obtained was 32% after 90 minutes.

EXAMPLE 10

The procedure was the same as in Example 5, but the reaction was carried out in the presence of V$_2$O$_5$ instead of VOSO$_4$. The yield of citral obtained was 33% after 220 minutes.

EXAMPLE 11

The procedure was the same as in Example 5, but the reaction was carried out in the presence of $4\times10^{-6}$, $4\times10^{-5}$ (Example 5) or $4\times10^{-4}$ moles of VOSO (reckoned as metal). The measured yields of citral were as follows:

| Time (min) | $4 \times 10^{-6}$ | TY (%) $4 \times 10^{-5}$ | $4 \times 10^{-4}$ |
|---|---|---|---|
| 15 | | | 45 |
| 30 | 2.5 | 45 | |
| 345 | 32 | | |

A decrease in the rate of reaction was observed with the decrease in the quantity of catalyst, but the true yield of citral was not effected.

EXAMPLE 12

The procedure was the same as in Example 5, but the reaction was carried out in the presence of methylene chloride instead of chlorobenzene and at a temperature of 37° C. Under these conditions, the yield of citral obtained was 61% after 55 minutes

EXAMPLE 13

The procedure was the same as in Example 5, but the reaction was carried out in the presence of a 10:1 (volume/volume) hexane/chlorobenzene mixture as a solvent, and at a temperature of approximately 45° C. Under these conditions, the yield of citral was 45% after 4 hours.

EXAMPLE 14

The procedure was the same as in Example 5, but the reaction was carried out in the presence of a 10:1 (volume/volume) pentane methylene chloride mixture and, at a temperature of 30° C. for 21 hours.
Under these conditions, the yield of citral was 61%.

EXAMPLE 15

The procedure was the same as in Example 5, but the reaction was carried out in the presence of methanol, ethyl acetate or toluene and, at a temperature of approximately 60° C. The yields obtained were as follows:
in methanol: 18% of citral after 1 hour
in toluene: 43% of citral after 1 hour
in AcOet: 38% of citral after 4 hours

EXAMPLE 16

The procedure was the same as in Example 5, but the reaction was carried out in the presence of tert-butyl methyl ether at 50° C. The yield obtained was 43% after 2 hours.

EXAMPLE 17

The procedure was the same as in Example 5, but the reaction was carried out in the presence of sulphuric acid. The pH of the reaction medium was adjusted to a value between 4.5 and 5. The yield of citral obtained was 32% after 3 hours.

EXAMPLE 18

The procedure was the same as in Example 5. The following three solutions were charged in parallel:

Solution 1

2.025 g of an aqueous solution of N,N-diethylgeranylamine N-oxide at a concentration of 67%,
30.8 mg of VOSO$_4$ (containing 22.75% of vanadium),
2.57 g of benzoic acid,
12 ml of water,
69 ml of methylene chloride, and
314 mg of undecane as an internal standard.

The pH of the solution was approximately 5.
Yield of citral after one hour at 38° C. was 63%.

Solution 2

0.682 g of an aqueous solution of N,N-diethylgeranylamine N-oxide at a concentration of 67%,
10.6 mg of VOSO$_4$ (containing 22.75% of vanadium),
0.322 g of formic acid,
4 ml of water,
23 ml of methylene chloride, and
102 mg of undecane as an internal standard.

The pH of the solution was approximately 2.1–3.
Yield of citral after 22 hours at 38° C. was 62%

Solution 3

0.691 g of an aqueous solution of N,N-diethylgeranylamine N-oxide at a concentration of 67%,
10.7 mg of VOSO$_4$ (containing 22.75% of vanadium),
0.661 mg of tartaric acid,
4 ml of water,
33 ml of methylene chloride, and
118 mg of undecane as an internal standard The pH of the solution was approximately 2.4.
Yield of citral after 4 hours at 38° C. was 61%.

EXAMPLE 19

The procedure was the same as in Example 5, but the reaction was carried out in the presence of an organic acid and an inorganic acid. For this example, the apparatus was equipped with a device for injecting the second acid (0.5M HCl solution at a flow rate of 0.7 ml/h).
The following were charged into the flask:
0.687 g of the aqueous solution of N,N-diethylgeranylamine N-oxide at a concentration of 67%, 10.5 mg of VOSO$_4$,
0.12 g of acetic acid,
4 ml of water, and
23 ml of methylene chloride.

The mixture was heated to 38° C. and 2.1 mls of the 0.5M HCl solution were injected over a period of 90 minutes. The pH was maintained between 4.2 and 4.5.

After 4 hours and 40 mins., the yield of citral was 60%.

EXAMPLE 20

The procedure was the same as in Example 19. The following were charged into the flask:
0.675 g of the aqueous solution of N,N-diethylgeranylamine N-oxide at a concentration of 67%,
10.5 mg of VOSO$_4$,
87.6 mg of crotonic acid,
4 ml of water, and
23 ml of methylene chloride.

The mixture was heated to 38° C. and 2.3 mls of the 0.5M HCl solution was injected over a period of 180 minutes. The pH was maintained between 4.5 and 5.

After 3 hours and 30 mins., the yield of citral was 51%.

EXAMPLE 21

The procedure was the same as in Example 5. but the reaction was carried out using a 10:1 (volume/volume) pentane/methylene chloride mixture as a solvent at a temperature of 30° C., and NH$_4$VO$_3$ as catalyst. The yield of citral obtained was 50% after 90 minutes.

EXAMPLE 22

This example illustrates the use of catalysts, derived from vanadium, on a support.

The procedure was the same as in Example 5. The following were charged into the flask:
0.68 g of the aqueous solution of N,N-diethylgeranylamine N-oxide at a concentration of 67%,
117 mg of 3% V$_2$O$_5$ on SiO$_2$,
0.426 g of acetic acid,
4 ml of water, and
23 ml of methylene chloride.
The mixture was heated to 37° C. The yield of citral was 60% after 3 hours.

EXAMPLE 23

The procedure was the same as in Example 22. The following were charged into the flask:
0.68 g of the aqueous solution of N,N-diethylgeranylamine N-oxide at a concentration of 67%,
36.9 mg of 10% V$_2$O$_5$ on alumina,
0.432 g of acetic acid,
4 ml of water, and
23 ml of methylene chloride The mixture was heated to 37° C. The yield of citral was 60% after 3 hours.

EXAMPLE 24

The procedure was the same as in Example 5. The following were charged to the flask:
2.67 g of an aqueous solution containing 1.51 g of N,N-dimethylbenzylamine N-oxide,
25 ml of chlorobenzene,
12.5 ml of water containing 10% of acetic acid,
0.5 g of undecane, and
0.05 g of vanadyl sulphate (containing 22.75% of vanadium).

The mixture was heated to reflux at 89° C. and the progress of the reaction was monitored by chromatography. After 15 minutes, the yield of benzaldehyde present in the organic layer was 63%. The reaction was stopped after 135 minutes and, after extraction of the aqueous layer with 2×15 ml of chlorobenzene, benzaldehyde was obtained in a yield of 69%.

EXAMPLE 25

The procedure was the same as in Example 5. The following were charged into the flask:
2.7 g of an aqueous solution containing 1.33 g of N,N-diethylprenylamine N-oxide,
1.2 ml of acetic acid, and
49 mg of vanadyl sulphate (containing 22.75% of vanadium).

The mixture was heated to reflux at 62° C. for 4 hours. After cooling, and separation after settling had taken place, the product was extracted with 2×25 ml of hexane, saturating the aqeuous layer with NaCl. The assay of prenal in the combined hexane phases by gas chromatography gave a 65% yield relative to the N-oxide.

EXAMPLE 26

A reactor was charged, in the following order, with:
4.4 g of an aqueous solution containing 15 mmol of N,N-dimethyl-ortho-hydroxybenzylamine N-oxide,
0.002 eq of VOSO$_4$,
1.1 eq of acetic acid, and
20 ml of ethyl acetate.

The mixture was heated to 60° C. for 5 hours and, after cooling, the aldehyde formed was assayed by GC. A true yield of 26% was obtained.

EXAMPLE 27

A 50-ml reactor equipped with a condenser, a thermometer, a pH-meter electrode and a stirrer was charged with:

| | |
|---|---|
| undecane (internal standard) | 500 mg |
| NH$_4$VO$_3$ | 23.5 mg |
| acetic acid | 0.3 g |
| water | 4 ml |
| hexane | 20 ml |

The mixture was heated to 60° C. and 3.38 g of N,N-diethylgeranylamine N-oxide and 5 ml of hexane were added. After mins., introduction began using a syringe driver, of 1N sulphuric acid (flow rate 1.7 ml/h) so as to maintain the pH of the solution at approximately 4.5. After 2 hours and 40 mins., a volume of 4.6 ml of 1N sulphuric acid had been introduced and the yield of citral was 45%.

EXAMPLE 28

The procedure was the same as in Example 26. The following were charged into the reactor:

| | |
|---|---|
| undecane | 112 mg |
| VOSO$_4$ | 10.5 mg |
| crotonic acid | 87.6 mg |
| water | 4 ml |
| methylene chloride | 20 ml |

The mixture was heated to 38° C. and 675 mg of N,N-diethylgeranylamine N-oxide and 3 ml of methylene chloride were added. After 2 mins., introduction began using a syringe driver, of 0.5M hydrochloric acid (flow rate 1.7 ml/h) so as to maintain the pH of the solution at approximately 4.5. After 3 hours and 30 minutes, a volume of 2.3 ml of 0.5M hydrochloric acid had been introduced and the yield of citral was 51%.

EXAMPLE 29

A 50-ml three-necked flask equipped with a condenser, a thermometer, a pH-meter electrode and a stirrer was charged with:

| | |
|---|---|
| undecane (internal standard) | 506 mg |
| $NH_4VO_3$ | 12 mg |
| acetic acid | 1.2 g |
| water | 4 ml |
| hexane | 20 ml |

The mixture was heated to 60° C. and 3.37 g of N,N-diethylgeranylamine N-oxide and 5 ml of hexane were added. The mixture was then heated for approximately 1 hour.

After cooling, the organic layer was removed, and was evaporated and analyzed in order to determine its citral content.

The following were charged into the aqueous phase: undecane, N-oxide, hexane (same quantities as above) and a supplementary amount of acetic acid (0.6 g). The mixture was then heated for 1 hour and the procedure was thereafter as before. Nine conversions were performed in this manner on the same catalytic lower layer. The yields of citral are given in the following table:

| Charge | Time (h) | Citral yield |
|---|---|---|
| 1 | 1 | 53.6 |
| 2 | 1 | 47.2 |
| 3 | 1.30 | 43.7 |
| 4 | 1 | 46.1 |
| 5 | 1 | 46.7 |
| 6 | 1 | 46.1 |
| 7 | 1.45 | 46 |
| 8 | 2.15 | 44.6 |
| 9 | 1.10 | 47 |

EXAMPLE 30

0.2 g (0.03 mol) of lithium metal and 20% of the total quantity (1.23 mol) of diethylamine were placed in a round-bottomed flask. The reactor was heated to reflux for one hour. A mixture composed of 95% myrcene, 143 g (1 mol), and the remaining 80% of the diethylamine, 72.4 g, was run into the reactor over a period of 1 hour. The reaction was left refluxing for 5 hours. After cooling, 5 g of water were added. The excess diethylamine, the unreacted myrcene and the water were removed by distillation (at 70° C. and at 27 mm of mercury). A residue of 176.7 g was obtained, and placed under a $CO_2$ atmosphere. 100 g of 30% hydrogen peroxide was added at 60° C. over a period of 2 hours. The mixture was maintained at this temperature for 2 hours. 271 g of crude N-oxide was thereby obtained. These 271 g of N-oxide were employed in the conversion reaction by adding 320 g of water, 168 g of acetic acid (2.8 mol), 1.88 g (0.016 mol) of ammonium vanadate and 2000 ml of hexane. The reaction mixture was heated to 60° C. for 30 minutes. After cooling, the organic layer was separated after settling had taken place. The citral was assayed by GC with internal standardization. 64.6 g (0.42 mol) of citral were obtained which is equivalent to a 42% yield relative to myrcene.

The intermediate yields are given in the following table:

| | Number of moles | TY of the step | TY/myrcene |
|---|---|---|---|
| MYRCENE | 1 | — | — |
| DEGA | 0.79 | 79% | 79% |
| N-OXIDE | 0.68 | 86% | 68% |
| CITRAL | 0.42 | 62% | 42% |

TY = true yield
DEGA = diethylgeranylamine

We claim:

1. A process for converting a tertiary amine N-oxide to an aldehyde comprising
reacting a tertiary amine N-oxide of the formula:

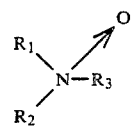

in which $R_1$, $R_2$, and $R_3$, which may be the same or different, are linear, branched or cyclic alkyl, allyl or alkenyl groups or benzyl groups, which groups, substituted or unsubstituted, contain 1 to 30 carbon atoms and in which formula $R_1$ and $R_2$ together can form a ring; in the presence of a catalytic quantity of at least one vanadium containing salt.

2. The process according to claim 1, wherein the reaction is carried out in the presence of a solvent.

3. The processing according to claim 1, wherein $R_1$ and $R_2$, which may be the same or different, are linear or branched alkyl groups containing 1 to 4 carbon atoms and which, together, can form a ring.

4. The process according to claim 3, wherein $R_1$ and $R_2$, which may be the same or different, are methyl or ethyl group.

5. The process according to claim 1, wherein $R_3$ is a substituted or unsubstituted, linear or branched allyl group having between 3 and 30 carbon atoms.

6. The process according to claim 5, wherein $R_3$ contains a ring.

7. The process according to claim 5, wherein $R_3$ contains one or more hetero atoms.

8. The process according to claim 1, wherein $R_3$ is a substituted or unsubstituted benzyl group containing up to 30 carbon atoms.

9. The process according to claim 8, wherein $R_3$ contains one or more hetero atoms.

10. The process according to claim 5, wherein $R_3$ is an allyl group containing between 3 and 15 carbon atoms.

11. The process according to claim 1, wherein the amine N-oxide is selected from N,N-dialkylprenylamine N-oxide, N,N-dialkylgeranylamine N-oxide, N,N-dialkylbenzylamine N-oxide or N,N-dialkyl-(2,6,6-trimethyl-1-cyclohexenyl)methanamine N-oxide.

12. The process according to claim 1, wherein the amine N-oxide is selected from N,N-diethylprenylamine N-oxide, N,N-diethylgeranylamine N-oxide, N,N-diethyl-(2,6,6-trimethyl-1-cyclohexenyl)methanamine N-oxide or N,N-dimethyl-ortho-hydroxybenzylamine N-oxide.

13. The process according to claim 1, wherein the mole ratio of vanadium salt, reckoned as metal to N-oxide is between 0.0001 and 0.5.

14. The process according to claim 13, wherein the mole ratio is between 0.001 and 0.1.

15. The process according to claim 2, wherein the solvent is selected from hydrocarbons, ethers, esters, alcohols, aromatic solvents or halogenated solvents.

16. The process according to claim 15, wherein the solvent is selected from pentane, hexane, ethyl acetate, methyl tert-butyl ether, chlorobenzene, methylene chloride, toluene, xylene, benzene or methanol.

17. The process according to claim 1, wherein the salt has a high oxidation number.

18. The process according to claim 17, wherein the vanadium salt is selected from $V_2O_5$, $NH_4VO_3$, $VOSO_4$, vanadyl acetylacetonate $VO(AcAc)_2$ or an alkyl vanadate.

19. The process according to claim 18, wherein the vanadium salt is an alkyl vandanate selected from triethanolamine orthovanadate or octadecyl orthovanadate $VO(OC_{18}H_{37})_3$.

20. The process according to claim 1, wherein the pH of the reaction medium is adjusted by adding an organic or inorganic acid or both.

21. The process according to claim 23, wherein the pH of the reaction medium is adjusted by adding a carboxylic acid.

22. The process according to claim 1, wherein the reaction medium further contains, per mole of N-oxide, between 0.05 and 2 liters of water and a volume of solvent of between 0 and 20 liters.

23. The process according to claim 22, wherein the volume of solvent of between 0.5 and 10 liters.

24. The process according to claim 1, wherein the pH is adjusted to a value of between 4 and 7.

25. The process according to claim 1, wherein the temperature is between room temperature and 150° C.

26. The process according to claim 1 further comprising recovering the aldehyde in an organic phase and a resulting secondary amine in an aqueous phase.

27. A process for producing unsaturated aldehyde comprising the following steps which are performed without isolating reaction intermediates,
condensing as reactants a conjugated diene and a secondary amine to obtain a tertiary amine;
oxidizing the tertiary amine with an oxidizing agent to obtain a tertiary amine N-oxide; and
reacting the tertiary amine N-oxide obtained in the presence of a catalytic quantity of at least one vanadium containing salt, to obtain an unsaturated aldehyde.

28. The process according to claim 27, wherein, the conjugated diene is selected from substituted or unsubstituted, linear, branched or cyclic alkenyl groups containing 4 to 30 carbon atoms.

29. The process according to claim 28, wherein the conjugated diene is selected from myrcene, isoprene, butadiene, farnesene or phytadiene.

30. The process according to claim 27, wherein the secondary amine is of the formula $HNR_1R_2$ in which $R_1$ and $R_2$, which may the same or different, are linear, branched or cyclic alkyl or alkenyl groups or benzyl groups, which groups, substituted or unsubstituted, contain 1 to 30 carbon atoms, in which $R_1$ and $R_2$ together can form a ring.

31. The process according to claim 27, wherein during the condensing step a catalyst selected from alkali metals is added.

32. The process according to claim 27, wherein the mole ratio of amine to diene is between 0.1 and 5.

33. The process according to claim 32, wherein the mole ratio of amine to diene is between 0.5 and 2.

34. The process according to claim 27, wherein the condensing step is performed at a temperature between room temperature and the refluxing temperature of the reactants.

35. The process according to claim 27, wherein during the oxidizing step, hydrogen peroxide is added as an oxidizing agent.

* * * * *

UNITED STATES PATENT AND TRADEMARK OFFICE
CERTIFICATE OF CORRECTION

PATENT NO. : 5,155,277
DATED : October 13, 1992
INVENTOR(S) : Pierre Chabardes, et. al.

It is certified that error appears in the above-indentified patent and that said Letters Patent is hereby corrected as shown below:

On the Title page, item [76], inventor's names should be deleted--"Sainte Foy Les, Saint Genis and change Lyons to --Lyon--;

Column 12, Claim 3, line 37, change "processing" to --process--;
Column 13, Claim 21, line 30, change "23" to --20--;.
Column 13, Claim 23, line 39, delete "of" (second occurrence) and insert--is--
Column 14, Claim 27, line 14, change "aldehyde" to --aldehydes--.

Signed and Sealed this

Fifteenth Day of March, 1994

Attest:

BRUCE LEHMAN

*Attesting Officer*  *Commissioner of Patents and Trademarks*